United States Patent [19]

Kidani et al.

[11] 4,256,652

[45] Mar. 17, 1981

[54] PLATINUM COMPLEX

[75] Inventors: Yoshinori Kidani, 2-1, Mataho-cho, Nishi-ku, Nagoya-shi, Aichi-ken, Japan; Masahide Noji, Nagoya, Japan

[73] Assignee: Yoshinori Kidani, Aichi, Japan

[21] Appl. No.: 46,628

[22] Filed: Jun. 8, 1979

Related U.S. Application Data

[62] Division of Ser. No. 941,559, Sep. 12, 1978.

[30] Foreign Application Priority Data

Sep. 12, 1977 [JP] Japan ................................ 52/108921

[51] Int. Cl.$^3$ .............................................. C07F 15/00
[52] U.S. Cl. ................................ 260/429 R; 424/287
[58] Field of Search ................................... 260/429 R

[56] References Cited

U.S. PATENT DOCUMENTS

4,115,418  9/1978  Gale et al. ...................... 260/429 R

OTHER PUBLICATIONS

Kidani et al, Gann 67 921–922 (1976).
Kidani et al, J. Clin. Hemat. and Oncol 7 197–209 Jan. 1977.
Speer et al, Journal of Clinical Hematology and Oncology, V8, (2) pp. 44 to 50 (1978).
Leh et al, J. Pharmaceutical Sciences, 65 (3) pp. 315–328 (1976).

*Primary Examiner*—Helen M. S. Sneed
*Attorney, Agent, or Firm*—Fitzpatrick, Cella, Harper & Scinto

[57] ABSTRACT

Cis-platinum (II) complexes wherein platinum (II) coordinates 1,2-diamino-cyclohexane (cis-, trans-l-or trans-d-) are disclosed. The complexes exhibit anti-tumor activity.

1 Claim, No Drawings

PLATINUM COMPLEX

This is a division of application Ser. No. 941,559 filed Sept. 12, 1978.

BACKGROUND OF THE INVENTION

The present invention relates to new platinum (II) complexes.

Heretofore, many reports have been made about platinum (II) complexes and the anti-tumor activity thereof, e.g. [Chem. Biol. Interaction, vol. 5, 415–424 (1972), Bioinorg. Chem. vol. 2, 187–210 (1973). Res. Commun. Chem. Pathol. Pharacol. vol. 7, 529–538, etc.]. The present inventors, while studying cis-platinum (II) complexes of 1,2-diamino-cyclohexane (hereinafter referred to as "dac"), succeeded to resolve dac, which is used as a starting compound, into three isomers, i.e., cis-, trans-l- and trans-d-; synthesized cis-platinum (II) complexes using these isomers and found that these complexes have anti-tumor activity. These complexes, their synthesis and utility are disclosed in U.S. Patent Application Ser. No. 775,216 filed on Mar. 7, 1977, now abandoned.

It has now been found that various other cis-platinum (II) complexes may be synthesized using the three isomers of dac as a starting compound; and these complexes exhibit strong anti-tumor activity.

SUMMARY OF THE INVENTION

In accordance with the present invention, novel platinum (II) complexes represented by the general formula (I)

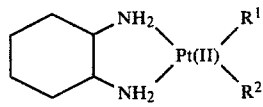

wherein $R^1$ and $R^2$ are the same and represent $Br^-$, $I^-$, $NO_3^-$, $BrCH_2CO_2^-$, or

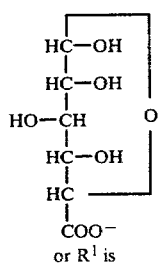

or $R^1$ is

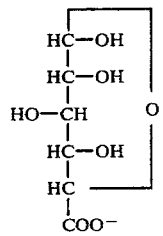

and $R^2$ is $No_3^-$, or $R^1$ and $R^2$ combine to form $SO_4^-$ or

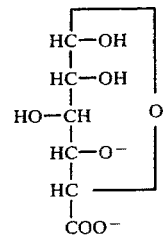

and the stereoisomerism of 1,2-diaminocyclohexane is cis-, trans-l- or trans-d-. The complexes of the present invention have anti-tumor activity.

DESCRIPTION OF THE INVENTION

The novel complexes of the invention are prepared by applying known methods, such as the methods disclosed in Journal of Pharmaceutical Sciences 65, 315–328 (1976). For example:

(1) $Pt(II)(dac)X_2$ is prepared by reacting $K_2PtX_4$ (X represents a halogen) with dac.

(2) $Pt(II)(dac)I_2$ and $Pt(II)(dac)Br_2$ are prepared by reacting $Pt(II)(dac)Cl_2$, which is obtained by the method (1), with KI and KBr respectively.

(3) $Pt(II)(dac)(NO_3)_2$ and $Pt(II)(dac)SO_4$ are prepared by reacting $Pt(II)(dac)X_2$ with silver nitrate and silver sulfate respectively.

(4) $Pt(II)(dac)Br_2$, glucuronate of $Pt(II)(dac)$ and bromoacetate of $Pt(II)(dac)$ are prepared by reacting $Pt(II)(dac)(NO_3)_2$ obtained by method (3) with KBr, sodium glucuronate and bromoacetic acid respectively.

The above reactions are carried out in water, if necessary, with heating (about 90° C.) or under interception of light. The reactions are usually completed in 3 to 48 hours to form generally white to yellow precipitates. The precipitates are recrystallized from 0.1 N HCl, or the like, whereby the desired products may be obtained in crystalline form.

This method is also described in the above-indentified U.S. Patent Application Ser. No. 775,216, which description is expressly incorporated herein by reference.

Diamines used in the present invention are cis-trans-l- or trans-di- isomers of dac. The process for preparation of the three isomers of dac is described in the above-mentioned U.S. Patent Application Ser. No. 775,216 which description is also expressly incorporated herein.

Representative compounds of the cis-platinum (II) complex of the present invention and their elementary analysis values are set forth respectively in the following Tables 1 and 2.

TABLE 1

| Compound No. | Compound | Example No. |
|---|---|---|
| 1 | cis-Pt(cis-dac)Br$_2$ | 1 |
| 2 | cis-Pt(trans-d-dac)Br$_2$ | 1 |
| 3 | cis-Pt(trans-d-dac)Br$_2$ | 1 |
| 4 | cis-Pt(cis-dac)I$_2$ | 2 |
| 5 | cis-Pt(trans-d-dac)I$_2$ | 2 |
| 6 | cis-Pt(trans-d-dac)I$_2$ | 2 |
| 7 | cis-Pt(cis-dac) (NO$_3$)$_2$ | 3 |
| 8 | cis-Pt(trans-d-dac) (NO$_3$)$_2$ | 3 |
| 9 | cis-Pt(trans-d-dac) (NO$_3$)$_2$ | 3 |
| 10 | cis-Pt(cis-dac) (BrCH$_2$CO$_2$)$_2$ | 4 |
| 11 | cis-Pt(trans-d-dac) (BrCH$_2$CO$_2$)$_2$ | 4 |
| 12 | cis-Pt(trans-d-dac) (BrCH$_2$CO$_2$)$_2$ | 4 |
| 13 | cis-Pt(cis-dac)SO$_4$ | 5 |
| 14 | cis-Pt(trans-d-dac)SO$_4$ | 5 |

TABLE 1-continued

| Compound No. | Compound | Example No. |
|---|---|---|
| 15 | cis-Pt(trans-d-dac)SO$_4$ | 5 |
| 16 | cis-Pt(cis-dac) (D-GlucH)NO$_3$ . 2H$_2$O | 6 |
| 17 | cis-Pt(trans-d-dac) (D-GlucH)NO$_3$ . 2H$_2$O | 6 |
| 18 | cis-Pt(trans-d-dac) (D-GlucH)NO$_3$ . 2H$_2$O | 6 |
| 19 | cis-Pt(cis-dac) (D-GlucH)$_2$ . 3H$_2$O | 7 |
| 20 | cis-Pt(trans-d-dac) (D-GlucH)$_2$ . 3H$_2$O | 7 |
| 21 | cis-Pt(trans-d-dac) (D-GlucH)$_2$ . 3H$_2$O | 7 |

In the foregoing Table and elsewhere herein the following abbreviations are used:

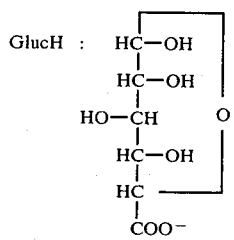

GlucH :

TABLE 2

| Compound No. | Elementary analysis | | | | | |
|---|---|---|---|---|---|---|
| | Found (%) | | | Calculated (%) | | |
| | C | H | N | C | H | N |
| 1 | 15.63 | 3.15 | 6.20 | | | |
| 2 | 15.40 | 2.93 | 6.17 | 15.36 | 3.01 | 5.97 |
| 3 | 15.42 | 2.80 | 5.98 | | | |
| 4 | 12.70 | 2.56 | 5.05 | | | |
| 5 | 12.69 | 2.49 | 5.09 | 12.80 | 2.51 | 4.97 |
| 6 | 12.84 | 2.54 | 5.10 | | | |
| 7 | 16.82 | 3.34 | 12.56 | | | |
| 8 | 16.93 | 3.39 | 12.54 | 16.63 | 3.26 | 12.93 |
| 9 | 16.79 | 3.30 | 12.68 | | | |
| 10 | 19.60 | 2.99 | 4.90 | | | |
| 11 | 19.59 | 3.10 | 4.98 | 20.52 | 3.10 | 4.79 |
| 12 | 19.76 | 3.03 | 4.99 | | | |
| 13 | 18.08 | 3.70 | 7.10 | | | |
| 14 | 17.93 | 3.67 | 6.79 | 17.78 | 3.48 | 6.91 |
| 15 | 17.42 | 3.65 | 6.90 | | | |
| 16 | 23.21 | 4.45 | 6.82 | | | |
| 17 | 23.45 | 4.72 | 6.95 | 24.00 | 4.53 | 7.00 |
| 18 | 23.18 | 4.60 | 7.03 | | | |
| 19 | 27.27 | 4.55 | 3.45 | | | |
| 20 | 28.25 | 4.67 | 3.53 | 28.84 | 5.11 | 3.74 |
| 21 | 27.80 | 4.60 | 3.52 | | | |

Cis-platinum (II) complexes of the present invention exhibit anti-tumor activity upon experimental tumors induced in mice, such as P388, S180A and L1210.

The cis-platinum (II) complexes also exhibit anti-microbial activity and are, therefore, also useful as disinfectants for cleaning and sterilizing surfaces and the like.

As chemotherapeutic agents, the cis-platinum (II) complexes of the invention may be administered orally, intra-muscularly or intravenously. They may be formulated as capsules, powders, pellets or injections in combination with various known pharmaceutical lubricants, binders and excipients.

Suitable dosage of the cis-platinum (II) complexes is about 1 to 400 mg/kg/day in animals.

The anti-tumor activity of the present cis-platinum (II) complexes is illustrated by the following representative experiments.

EXPERIMENT 1

In this experiment the activity against experimental tumor P388 in mice is tested.

Leukemia P388 cells were injected intraperitoneally to groups of CDF$_1$ mice (Number of transplanted cells was 10$^6$ per mouse); and on the first and fifth days after transplantation, the test compound was administered by intraperitoneal injection to the mice. The dosage and test compound are set forth in the following Tables 3 and 4.

The effect of the test compound was evaluated by means of extension of average survival period T/C % (average survival days of the groups administered with the test compound/average survival days of the control group). When the T/C % is equal to or more than 120%, the test compound is considered to be effective. The results are also shown in Tables 3 and 4.

TABLE 3

| Compound No. | Toxic Dose (mg/kg) | Optimum Dose | | MED | | T.I. |
|---|---|---|---|---|---|---|
| | | (mg/kg) | T/C (%) | (mg/kg) | T/C (%) | |
| 1 | 50 | 25 | 190 | 1.56 | 126 | 16 |
| 2 | 100 | 25 | 238 | ≦1.56 | 144 | ≧16 |
| 3 | 50 | 12.5 | 217 | 1.56 | 130 | 8 |
| 4 | ≧200 | 25 | 141 | 6.25 | 129 | 4 |
| 5 | ≧200 | ≧100 | 182 | 6.25 | 125 | ≧16 |
| 6 | ≧200 | ≧100 | 149 | 12.5 | 121 | ≧8 |
| 7 | ≧50 | 12.5 | 180 | ≦1.56 | 144 | ≧8 |
| 8 | 25 | 6.25 | 187 | ≦1.56 | 147 | ≧4 |
| 9 | 50 | 12.5 | 198 | ≦1.56 | 151 | ≧8 |
| 10 | 100 | 50 | 175 | 6.25 | 140 | 8 |
| 11 | 100 | 25 | 198 | ≦6.25 | 154 | ≧4 |
| 12 | ≧200 | ≧100 | 190 | ≦6.25 | 143 | ≧16 |
| 13 | 25 | 6.25 | 202 | 0.78 | 122 | 8 |
| 14 | 12.5 | 6.25 | 212 | 1.56 | 140 | 4 |
| 15 | 25 | 6.25 | 200 | 0.39 | 124 | 16 |
| 16 | 50 | 25 | 208 | 1.56 | 139 | 16 |
| 17 | 50 | 25 | 203 | 0.39 | 124 | 64 |
| 18 | 50 | 25 | 188 | 1.56 | 120 | 16 |
| 19 | ≧200 | 100 | 191 | 6.25 | 134 | ≧16 |
| 20 | 100 | 50 | 224 | 3.12 | 141 | 16 |
| 21 | 100 | 50 | 181 | 6.25 | 123 | 8 |

MED: The lowest dose where T/C % exceeds 120%
T.I.: Therapeutic Index (Optimum Dose/MED)

TABLE 4

| Compound No. | Dose (mg/kg) | | |
|---|---|---|---|
| | 25 | 12.5 | 6.25 |
| 1 | 190 | 188 | 167 |
| 2 | 238 | 201 | 190 |
| 3 | 90 | 217 | 203 |
| 4 | 141 | 139 | 129 |
| 5 | 159 | 146 | 125 |
| 6 | 141 | 121 | 119 |
| 7 | 108 | 180 | 171 |
| 8 | 65 | 90 | 180 |
| 9 | 173 | 198 | 162 |
| 10 | 168 | 164 | 151 |
| 11 | 198 | 163 | 150 |
| 12 | 172 | 158 | 141 |
| 13 | 60 | 134 | 202 |
| 14 | 0 | 83 | 212 |
| 15 | 0 | 93 | 200 |
| 16 | 208 | 184 | 170 |
| 17 | | 203 | 187 |
| 18 | 188 | 180 | 147 |
| 19 | 178 | 153 | 134 |
| 20 | 189 | 176 | 147 |
| 21 | 170 | 133 | 123 |

EXPERIMENT 2

In this experiment the activity against experimental tumor ascites-type S180A in mice is tested.

Ascites-type sarcoma 180A were transplanted intraperitoneally to ddN mice. The test compound was then interperitoneally injected every day from one to five days. The resulting ascites in the mice were sampled to evaulate the anti-tumor activity of the test compound by means of the growth rate of the tumor, T/C % (groups administered with the test compound/control group).

The results are shown in Table 5 below wherein the designations "+", "++" and "+++" mean 65-41%, 40-11% and 10-0% of the T/C % respectively and the term "toxic" is used in the case where all the mice died.

TABLE 5

| Compound No. | Dose (mg/kg) | T/C (%) | Effect |
|---|---|---|---|
|  | 3 | 41 | + |
|  | 10 | 41 | + |
| 2 | 3 | 29 | + + |
| 3 | 3 | 22 | + + |
| 7 | 3 | 10 | + + + |
|  | 10 | — | Toxic |
| 8 | 3 | 13 | + + |
|  | 10 | — | Toxic |
| 9 | 1 | 13 | + + |
|  | 3 | — | Toxic |
| 10 | 10 | 43 | + |
| 11 | 3 | 30 | + + |
| 12 | 10 | 25 | + + |
| 13 | 3 | 7 | + + + |
|  | 10 | — | Toxic |
| 14 | 3 | 5 | + + + |
|  | 10 | — | Toxic |
| 15 | 3 | — | Toxic |
|  | 10 | — | Toxic |

EXPERIMENT 3

In this experiment, the activity against experimental tumor Leukemia L-1210 in mice is tested.

Leukemia L-1210 cells were transplanted intraperitoneally (Number of transplanted cells was $10^6$ per mouse) to $CDF_1$ mice. The test compound was then administered intraperitoneally to the mice on the first, fifth and ninth day after transplantation. The effect of the test compound was evaluated by means of extension of the average survival period T/C % (average survival days of the groups administered with the test compound/average survival days of the control group). When T/C % is equal to or more than 120%, the test compound is considered to be effective. The results are shown in Tables 6 and 7.

TABLE 6

| Compound No. | Toxic Dose (mg/kg) | Optimum Dose (mg/kg) | Optimum Dose T/C (%) | MED (mg/kg) | MED T/C (%) | T.I. |
|---|---|---|---|---|---|---|
| 1 | ≧50 | 25 | 188 | 6.25 | 151 | >4 |
| 2 | ≧50 | 25 | 229(1) | 0.78 | 128 | >32 |
| 3 | ≧50 | 6.25 | 252 | 1.56 | 140 | 4 |
| 7 | ≧25 | 12.5 | 253(2) | 0.39 | 138 | >32 |
| 8 | ≧25 | 6.25 | 335(3) | 0.39 | 134 | 16 |
| 9 | ≧25 | 6.25 | 287(2) | 0.39 | 120 | 16 |
| 13 | 25 | 6.25 | 180 | 0.78 | 131 | 8 |
| 14 | 12.5 | 3.12 | 189 | <0.78 | 156 | >4 |
| 15 | 12.5 | 3.12 | 219 | <0.78 | 152 | >4 |
| 16 | 100 | 50 | 212(2) | 6.25 | 130 | 8 |
| 17 | ≧100 | 12.5 | 313(4) | 1.56 | 136 | >8 |
| 18 | 50 | 25 | 313(2) | 1.56 | 130 | 16 |
| 19 | 200 | 25 | 154 | 6.25 | 129 | 4 |
| 20 | 200 | 50 | 330(2) | 6.25 | 141 | 8 |
| 21 | 50 | 25 | 274(1) | 6.25 | 191 | 4 |

TABLE 7

| Compound No. | Dose (mg/kg) | | | | | | | | |
|---|---|---|---|---|---|---|---|---|---|
|  | 100 | 50 | 25 | 12.5 | 6.25 | 3.12 | 1.56 | 0.78 | 0.39 |
| 1 | 13 | — | 188 | 184 | 151 | 115 | 113 | 110 | — |
| 2 | — | — | 229 (1) | 140 | 176 | 151 | 130 | 128 | — |
| 3 | — | — | (216) | 146 | 252 | 142 | 140 | 115 | — |
| 7 | — | — | — | 253 (2) | 166 | 140 | 319 (3) | 148 | 143 |
| 8 | — | — | — | 331 (4) | 335 (3) | 231 (1) | 189 | 144 | 134 |
| 9 | — | — | — | 269 (2) | 287 (2) | 186 | 186 (1) | 130 | 120 |
| 13 | — | — | — | 93 | (180) | 146 | 156 | 131 | 13 |
| 14 | — | — | — | 0 | (165) | 189 | 152 | 156 | — |
| 15 | — | — | — | 0 | 197 | 219 | 167 | 152 | — |
| 16 | — | (212) (2) | 196 | 148 | 130 | 113 | 110 | — | — |
| 17 | — | (129) (1) | 284 (3) | 313 (4) | 198 | 167 | 136 | — | — |
| 18 | — | 79 | (313) (2) | 221 | 218 (1) | 154 | 130 | — | — |
| 19 | 90 | 139 | 154 | 125 | 129 | — | — | — | — |
| 20 | 98 | 330 (2) | 269 (1) | 213 (1) | 141 | 114 | — | — | — |
| 21 | 74 | 83 | 274 (1) | 212 (1) | 191 (1) | — | — | — | — |

MED: Minimum Effective Dose, the lowest dose when T/C % exceeds 120%
T.I.: Therapeutic Index (Optimum Dose/MED)
Figures in parenthesis are toxic by the decrease of body weight.
Number in parenthesis, right hand side below, indicates the survivor to 6 mice The following representative examples illustrate preparation of cis-platinum (II) complexes of the present invention.

EXAMPLE 1

Cis-dibromo(1,2-diaminocyclohexane) platinum(II) complex

In this example, 0.43 g (1 mmol) of $[Pt(dac)(NO_3)_2]$ (dac is a cis-, trans-l- or trans-d-isomer) is dissolved in 20 ml of water with heating (about 90° C.) and then 1 g (8.4 mmol) of KBr is added to the solution. The mixture is stirred at room temperature to form a yellow precipitate. The reaction proceeds almost quantitatively and each platinum complex of isomers is obtained in a 90% yield.

EXAMPLE 2

Cis-diiodo(1,2-diaminocyclohexane) platinum(II) complex

In this example, 0.56 g (1.3 mmol) of $K_2[PtCl_4]$ is dissolved in 20 ml of water and to the solution there is added 2 g (12 mmol) of KI. The mixture is heated at 60° C. for 3 hours. To the resultant deep dark red solution 0.26 g (1.2 mmol) of cis-dac (H$_2$SO$_4$), or 0.22 g (1.2 mmol) of trans-l-dac (HCl)$_2$ or trans-d-dac (HCl)$_2$ is added. Then 5% (w/v) KOH solution is added to make the pH neutral to weakly alkaline and to form yellowish brown precipitates. The precipitate is then separated, washed with water and acetone and dried.

Yield: 85% (each complex of isomers)

EXAMPLE 3

Cis-dinitrato(1,2-diaminocyclohexane) platinum(II) complex

In this example, 1.14 g (3 mmol) of [Pt(dac)Cl$_2$] (dac is a cis-, trans-l- or trans-d-isomer) is suspended in 100 ml of water and to the suspension is added 1.02 g (3 mmol) of AgNO$_3$. The mixture is stirred at room temperature for 2 days under interception of light and the resultant AgCl is removed by filtration. Then, 5% (w/v) KCl solution is added to the filtrate little by little to remove unreacted AgNO$_3$. The solution free of Ag$^+$ is dried with heating under reduced pressure using an evaporator whereby the desired complexes are obtained as a yellowish white powder.

Yield: 80% (trans-l- or trans-d-complex) and 85% (cis-complex).

The [Pt(dac)Cl$_2$] used as a starting compound is prepared as follows:

An aqueous solution of 5 g of dac (a cis-, trans-l- or trans-d-isomer) and 18 g of K$_2$(PtCl$_4$) is allowed to react at room temperature for about 12 hours to precipitate yellow needle-like crystals. The crystals are obtained by filtration and recrystallized from 0.1 N HCl.

Yield: 73% (cis-complex) and 78% (trans-l- or trans-d-complex).

EXAMPLE 4

Cis-bisbromoacetato(1,2-diaminocyclohexane) platinum(II) complex

In this example, 0.43 g (1 mmol) of [Pt(dac)(NO$_3$)$_2$] (dac is a cis-, trans-l- or trans-d-isomer) is dissolved in water with heating and the solution is cooled in a refrigerator. Then, 1 g (7.2 mmol) of bromoacetic acid is added to the solution and the mixture is allowed to stand for 3 days under interception of light in the refrigerator. A white precipitate formed in the mixture is separated by filtration, washed with water and acetone and dried under reduced pressure at 30°-40° C.

Yield: 40% (cis-complex) and 45% (trans-l- or trans-d-complex).

EXAMPLE 5

Cis-sulfato(1,2-diaminocyclohexane) platinum(II) complex

In this example, 0.38 g (1 mmol) of [Pt(dac)Cl$_2$] (dac is a cis-, trans-l- or trans-d-isomer) is added to a solution of 0.35 g of silver sulfate in 100 ml of water. The mixture is stirred at room temperature for 2 days under interception of light. AgCl formed is removed by filtration and to the filtrate there is added 5% (w/v) KCl solution, little by little, to remove Ag$^+$. The filtrate is dried at 50°-60° C. under reduced pressure using an evaporator whereby the desired sulfato-complex is obtained as a yellowish white powder.

Yield: 80% (cis-complex) and 75% (trans-l- or trans-d-complex).

EXAMPLE 6

Cis-nitrato-D-glucuronato(1,2-diaminocyclohexane) platinum(II) complex

In this example, 0.22 g (0.5 mmol) of [Pt(dac)(NO$_3$)$_2$] (dac is a cis-, trans-l- or trans-d-isomer) is dissolved in 10 ml of water with heating and the solution is cooled to room temperature. Then, 0.12 g (0.5 mmol) of sodium glucuronate is added to the solution and the mixture is allowed to stand at room temperature for one week. The solution is then dried at 50°-60° C. under reduced pressure using an evaporator to obtain a yellow residue. The residue is washed with warm methanol to obtain the desired product.

Yield: 75% (cis-complex) and 70% (trans-l- or trans-d-complex).

EXAMPLE 7

Cis-bis-D-glucuronato(1,2-diaminocyclohexane) platinum(II) complex

In this example, 0.22 g (0.5 mmol) of [Pt(dac)(NO$_3$)$_2$] (dac is a cis-, trans-l- or trans-d-isomer) is dissolved in 10 ml of water with heating. After the solution is cooled to room temperature, 0.24 g (1 mmol) of sodium glucuronate is added thereto and the mixture is allowed to stand at room temperature for a week. The resultant solution is dried at 50°-60° C. under reduced pressure using an evaporator to obtain a yellow powder which is then washed with warm methanol and dried to obtain the desired product.

Yield: 70% (cis-, trans-l- or trans-d-complex).

Characteristic points of the infrared absorption spectra of the cis-platinum (II) complexes obtained in the above Examples are explained below.

Pt(dac)X$_2$: X=Br$^-$, I$^-$

Trans-dac in platinum complexes exhibits peaks due to $\nu$ NH$_2$ at 3280, 3200 and 3020 cm$^{-1}$. Cis-dac exhibits a peak due to $\nu$ NH$_2$ (asym) at 3250 cm$^{-1}$, which is a lower wave number shift than that of trans complexes, and exhibits two other peaks due to $\nu$ NH$_2$ at a wave number (i.e. 3200 and 3020 cm$^{-1}$) the same as trans-dac. A peak due to $\delta$ NH$_2$ is observed at 1570 cm$^{-1}$ in both isomers.

Geometrical isomers of dac in the complexes are distinguishable by the rocking mode of CH$_2$ which is observed at 900–1000 cm$^{-1}$. That is, only one absorption peak is observed in trans-dac, whereas three peaks are observed in cis-dac which is low in symmetry.

The above-mentioned spectrum characteristics of dac are applied in the following platinum complexes insofar as the peaks of dac do not overlap those of a leaving group.

Pt(dac)(NO$_3$)$_2$

Peaks due to $\nu$ NO$_3$ of coordinated NO$_3^-$ are observed at 1500, 1385, 1260–1300 and 990 cm$^{-1}$.

Geometrical isomers of dac are distinguishable in that the trans-isomer exhibits a weak absorption peak at 827 cm$^{-1}$, whereas the cis-isomer exhibits two weak but clear peaks at 915 and 940 cm$^{-1}$. There is not observed such difference as in halogeno-complexes in action of $\nu$ of NH$_2$ in 3000–4000 cm$^{-1}$.

Pt(dac)(SO$_4$)

Sulfato-complexes exhibit a broad absorption spectrum due to $\nu$ SO$_4$ at 1120, 1030 and 950 cm$^{-1}$.

Geometrical isomers of dac are poorly distinguished by spectrum at 900–1000 cm$^{-1}$ because their peaks overlap that of $\nu$ SO$_4$.

Pt(BrCH$_2$CO$_2$)$_2$(dac)

Existence of the monobromoacetate ion in complexes may be confirmed by the fact that a broad absorption band at 1620 and 1350 cm$^{-1}$ is attributable to $\nu$ CO$_2$.

Geometrical isomers of dac are distinguishable similarly as in halogeno-complexes by spectrum at 900–1000 cm$^{-1}$.

Pt(GlucH)NO$_3$(dac)

Peaks due to $\nu$ NH$_2$ and $\nu$ OH are observed respectively at 3100–3250 cm$^{-1}$ and 3300–3600 cm$^{-1}$. Peaks due to $\nu$ CO$_2$ (asym) and $\nu$ CO$_2$(sym) are observed respectively at 1600 cm$^{-1}$ and 1400 cm$^{-1}$. Peaks due to $\nu$ NO$_3$ are observed at 995, 1300 and 1500 cm$^{-1}$, whereby it is concluded that NO$_3^-$ is included in the complex.

Pt(GlucH)$_2$(dac)

A broad absorption band is observed at 3200–3400 cm$^{-1}$, which is attributed to the overlap of $\nu$ OH(-GlucH) with $\nu$ NH$_2$(dac). Peaks due to $\nu$ CO$_2$(asym) and $\nu$ CO$_2$(sym) are observed respectively at 1610 cm$^{-1}$ and 1400 cm$^{-1}$.

What is claimed is:

1. Cis-Pt(II)(trans-l-1,2-diaminocyclohexane)SO$_4$.